United States Patent [19]

Kondo et al.

[11] 4,301,026

[45] Nov. 17, 1981

[54] ANTIOXIDANT FOR CARBONACEOUS MATERIAL AND METHOD

[76] Inventors: Teruhisa Kondo, No. 28-8, Higashitoyonaka-cho, 1-chome, Toyonaka-shi, Osaka-fu; Jiro Ishiguro, Takesato-danchi 2-4-308, No. 89, Ooeda, Ooaza, Kasukabe-shi, Saitama-ken; Nobuatsu Watanabe, No. 136, Uguisu-dai, Nagaokakyo-shi, Kyoto-fu, all of Japan

[21] Appl. No.: 28,027

[22] Filed: Apr. 6, 1979

[51] Int. Cl.³ ............................................. C09K 15/32
[52] U.S. Cl. ............................................. 252/400 R
[58] Field of Search ................ 252/400 R; 423/448, 423/460, 275; 260/799; 536/107, 102, 103, 104, 121

[56] References Cited

U.S. PATENT DOCUMENTS 3,544,614  12/1970  Schwartz .................. 252/400 R
3,644,217  2/1972   Cyba ........................ 252/400 R

*Primary Examiner*—Benjamin R. Padgett
*Assistant Examiner*—J. L. Barr
*Attorney, Agent, or Firm*—Sprung, Felfe, Horn, Lynch & Kramer

[57] ABSTRACT

Novel metal salts of boric acid esters of saccharides have been found to be extremely useful for imparting a high oxidation-resistance to carbonaceous materials. The metal salts of the boric acid esters according to the present invention are water-soluble and can be easily formulated into aqueous solutions thereof. Therefore, the treatment of carbonaceous materials can be easily, simply done using an aqueous solution of the present metal salt of the boric acid ester.

5 Claims, No Drawings

ANTIOXIDANT FOR CARBONACEOUS MATERIAL AND METHOD

This invention relates to an antioxidant for carbonaceous materials. More particularly, the present invention is concerned with an antioxidant for carbonaceous materials which comprises a metal salt of a boric acid ester of a saccharide, and a process for the preparation of the same. The present invention is also concerned with a method of rendering a carbonaceous material resistant to oxidation.

Carbonaceous materials have widely been used as a heat resistant material for super high temperatures, in various industries. The carbonaceous materials, however, are still insufficient in oxidation-resistance, and the applications of the carbonaceous materials are limited.

With a view to improving the oxidation-resistance of carbonaceous materials, there have heretofore been proposed various methods.

One of the conventionally proposed methods consists of incorporating into a carbonaceous material a phosphorus-containing compound such as phosphoric acid or a phosphate of a metal, e.g., barium, aluminum, calcium or magnesium. Such a phosphorus-containing compound as the additive is not only strongly acidic but also susceptible to water and, hence, the treating operation for incorporation of the additive is troublesome and complicated. Furthermore, this conventional method cannot impart a sufficient oxidation-resistance to the treated carbonaceous materials.

In addition, there are also known a method in which a carbonaceous material is impregnated with alumina sol; a method in which a zinc phosphate glass is incorporated into a carbonaceous material; and a method in which a carbonaceous material is impregnated with alumina sol and then treated with a solution of respective organic esters of phosphoric acid and boric acid (e.g., triphenyl phosphate and triethyl borate) in an organic solvent such as methanol whereby there is formed a glassy material of the three-component system in the carbonaceous material. Any of those known methods, however, is not advantageous, because some of the antioxidants to be used have poor permeability for carbonaceous materials and there cannot be obtained a sufficient oxidation-resistance and because some of the antioxidants to be used should be used in the form of a solution of an organic solvent system, leading to problems of economics and environmental pollution.

The present inventors have made extensive and intensive researches. As a result, it has been found that specific water-soluble or comparatively water-soluble metal salts of organic boric acid esters are useful for imparting a high oxidation-resistance to carbonaceous materials and that the treatment of carbonaceous materials with such a novel antioxidant can be easily conducted, enabling the carbonaceous material to be highly resistant to oxidation by a simple operation. The present invention has been made, based on such novel findings.

Accordingly, it is an object of the present invention to provide a novel and excellent antioxidant for carbonaceous materials which is capable of imparting a high oxidation-resistance to carbonaceous materials.

It is another object of the present invention to provide an antioxidant of the character described, which is water-soluble or comparatively water-soluble and, therefore, can be easily handled.

It is still another object of the present invention to provide a process for the preparation of a novel antioxidant for carbonaceous materials as mentioned above.

It is a further object of the present invention to provide a method of rendering a carbonaceous material resistant to oxidation by the use of a novel antioxidant as mentioned above.

The foregoing and other objects, features and advantages of the present invention will be apparent to those skilled in the art from the following detailed description and appended claims.

Essentially, according to the present invention, there is provided an antioxidant for a carbonaceous material which comprises at least one metal salt of a boric acid ester of a member selected from the group consisting of a reduction product of a monosaccharide, a dimer of a monosaccharide and combinations thereof, said metal being a member selected from metals of the group II of the periodic table.

As examples of the reduction product of a monosaccharide, there can be mentioned sorbitol and mannitol which are reduction products of dextrose and D-fructose, respectively. The dimers of monosaccharides are those which are generally called "disaccharides", and include, for example, sucrose, maltose and lactose. Among metals of the group II of the periodic table, there may advantageously be employed magnesium, calcium, zinc, barium and the like. Such polyhydroxy compounds as the reduction products of monosaccharides and the dimers of monosaccharides (hereinafter, both often referred to simply as "saccharide") may be employed alone or in combination. The metals of the group II of the periodic table may also be employed alone or in combination.

The above-defined metal salts of boric acid esters of saccharides to be employed in the present invention are novel compounds. These novel compounds can be prepared by a process in which a saccharide that is a polyhydroxy compound as defined above is reacted with boric acid and the resulting boric acid ester of saccharide is then neutralized with a compound of a metal of the group II of the periodic table. The thus obtained metal salts of boric acid esters of saccharides are soluble or comparatively soluble in water as opposed to the salts of boric acid with metals of the group II of the periodic table which are insoluble or sparingly soluble in water. Therefore, the metal salts of boric acid esters of saccharides can be easily formulated into an aqueous solution thereof, and hence, can advantageously be used for the antioxidizing treatment of a carbonaceous material according to the present invention.

Accordingly, in another espect of the present invention, there is provided a process for the preparation of an antioxidant for a carbonaceous material which comprises reacting a member selected from the group consisting of a reduction product of a monosaccharide, a dimer of a monosaccharide and mixtures thereof with boric acid, and subsequently reacting the resulting boric acid ester with at least one compound of a metal selected from metals of the group II of the periodic table.

As representative examples of the compounds of metals of the group II of the periodic table, there can be mentioned oxides, hydroxides, carbonates and basic carbonates of magnesium, calcium, zinc and barium. As preferred examples of the basic carbonate, there can be mentioned $4MgCO_3 \cdot Mg(OH)_2 \cdot 5H_2O$, $3MgCO_3 \cdot Mg(OH)_2 \cdot 5H_2O$ and mixtures thereof.

In practicing the process of the present invention, a desired metal salt of a boric acid ester of a saccharide may be prepared as follows. A saccharide selected from the group consisting of a reduction product of a monosaccharide, a dimer of a monosaccharide and mixtures thereof is mixed with water. An amount of water to be used may be about 30 to 100% by weight, preferably about 50 to 60% by weight, based on the saccharide employed. To the resulting mixture or solution is added boric acid to effect esterification reaction. An amount of boric acid to be added may be about 0.5 to 2 moles, preferably about 0.5 to 1.5 mole, more preferably about 1.0 mole per mole of the saccharide employed. The esterification reaction may be conducted under the ordinary reaction conditions for esterification with dehydration. The reaction temperature may be about 105° to 130° C., preferably 110° to 120° C. The reaction period may vary depending on the reaction temperature, but may generally be within the range of about 2 to 5 hours. As the reaction product, there is obtained a boric acid ester of the saccharide in the form of a transparent, viscous liquid. The thus obtained boric acid ester is diluted with water so that there is obtained an aqueous solution of the ester having a solid concentration of 30 to 80% by weight, preferably 40 to 60% by weight. To the resulting aqueous solution of the boric acid ester is added a compound of a metal of the group II of the periodic table in an amount of about 1 to 3 moles (in terms of amount of metal oxide) per mole (in terms of amount of boric acid anhydride) of the boric acid ester. In this connection, it is noted that the content of boron in the boric acid ester can be easily, accurately determined because the boric acid ester formation is quantitative. The reaction temperature for the formation of a metal salt of the boric acid ester by the reaction between the boric acid ester and the metal compound is not critical, and the reaction may proceed sufficiently at about room temperature. If desired, however, the reaction may be effected at elevated temperatures, so that the rate of reaction can be advantageously increased. In general, the reaction for the formation of a metal salt of the boric acid ester may be conducted at temperatures ranging from about room temperature to about 100° C. By conducting the reaction, while stirring, for about 20 to 30 minutes, there is obtained a desired metal salt of a boric acid ester of a saccharide in the form of a transparent aqueous solution. The solid concentration of the thus obtained aqueous solution of a metal salt of a boric acid ester of a saccharide is varied depending on the atomic weight of the metal incorporated as the salt of the boric acid ester, but may in general be within the range of about 50 to about 60% by weight. The above-mentioned solid concentration can be easily determined by the so-called xylene method.

An explanation on the mechanism of the above-mentioned formation of a metal salt of a boric acid ester of a saccharide will now be given, referring, for example, to the case where sucrose is employed as the saccharide. As well known, sucrose is a polyhydroxy compound represented by the following formula

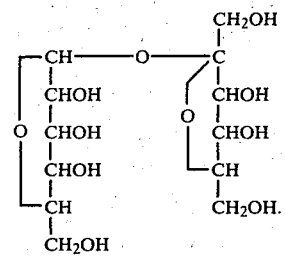

The hydroxyl group in sucrose is reacted with boric acid of the formula

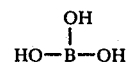

to effect esterification with dehydration, thereby forming an ester linkage represented by the formula

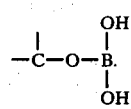

The formation of the ester linkage is believed to occur at one or some of the three —CH$_2$OH groups in sucrose. After formation of the ester linkage, the hydrogen moieties (acidic) in the above-mentioned boric acid ester structure are neutralized with a compound of a metal of the group II of the periodic table, which compound is selected from, for example, oxides, hydroxides, carbonates and basic carbonates of magnesium, calcium, zinc and barium. Thus, there is obtained a metal salt of a boric acid ester of sucrose which is a novel compound and useful as one of antioxidants for carbonaceous materials according to the present invention.

A metal salt of a boric acid ester of a saccharide prepared according to the process as mentioned above is completely water-soluble, where the molar ratio of the boric acid values to the saccharide values in the metal salt is 1(one) or less. Where the above-mentioned molar ratio is more than 1(one), the metal salt is not so completely water-soluble but partially dispersed in water (i.e., comparatively water-soluble). Even the metal salt which is comparatively water-soluble as mentioned above, however, can be used, without any trouble, in the form of an aqueous solution in which the metal salt is partially dispersed (hereinafter, such an aqueous solution is often referred to simply as "aqueous solution"), as the antioxidant according to the present invention and the intended purpose can be attained by the use of such a comparatively water-soluble metal salt.

As mentioned above, a metal salt of a boric acid ester of a saccharide prepared according to the process of the present invention is water soluble or comparatively water-soluble and, therefore, can be easily used in the form of an aqueous solution for impregnating carbonaceous materials therewith. When the carbonaceous material (e.g. graphite and carbon) impregnated with a metal salt of a boric acid ester of saccharide is heated, the metal salt is caused to form a two-component system glassy compound, namely a B$_2$O$_3$-metal oxide system compound. Such a two-component system glassy compound is chemically and firmly adsorbed onto the active sites in the interior of the carbonaceous material to form a caking structure. It is believed that the thus formed caking structure serves to effectively impart a high oxidation-resistance to the carbonaceous material.

Accordingly, in a further aspect of the present invention, there is provided a method of rendering a carbonaceous material resistance to oxidation which comprises contacting a carbonaceous material with an antioxidant comprising at least one metal salt of a boric acid ester of a member selected from the group consisting of a reduction product of a monosaccharide, a dimer of a monosaccharide and combinations thereof for a sufficient time for said antioxidant to permeate the carbonaceous material, said metal being a member selected from metals of the group II of the periodic table, and subjecting said carbonaceous material to heat-treatment.

In practicing the method of rendering a carbonaceous material resistant to oxidation, the contacting of a carbonaceous material with the antioxidant may be effected by impregnation. The impregnation may be conducted using a 3 to 30% by weight aqueous solution of a metal salt of a boric acid ester of a saccharide. The method for impregnation is not limited, and any of the ordinarily employed impregnation methods such as dipping, brushing, spraying, etc. can be utilized. From a viewpoint of efficiency of working, a dipping method may preferably be used. In the dipping method, pressure is not critical, and dipping may be conducted under atmospheric pressure, super atmospheric pressure or reduced pressure. Dipping time may be suitably within the range of about 30 minutes to several-ten hours. After a carbonaceous material is dipped in an aqueous solution of a metal salt of a boric acid ester of a saccharide, the content of the aqueous solution in the carbonaceous material may preferably be reduced to about 50% by weight by a suitable method such as suction filtration, centrifugation or the like. Subsequently, the carbonaceous material may be dried at temperatures of not higher than 100° C., and then subjected to heat-treatment at about 400° to about 1,300° C. Heating time may be varied depending on the heating temperature as well as the size of the carbonaceous material, but may generally be in the range of several seconds to ten and several hours. The carbonaceous material treated as mentioned above is imparted with excellent resistance to oxidation.

The present invention is further illustrated in more detail by the following examples which should not be construed to be limiting the scope of the present invention.

EXAMPLE 1

To 260 g(1 mole in terms of sorbitol) of SORBIT D-70 (trade name of a 70 weight % aqueous solution of sorbitol manufactured and sold by Towa Kasei Kogyo Kabushiki Kaisha, Japan) were added 61.8 g(1 mole) of boric acid. The resulting mixture was heated, while stirring, at 110° to 120° C. for 3 hours to effect esterification with dehydration. The thus obtained boric acid ester of sorbitol was diluted with water so as to form an aqueous solution of the boric acid ester which solution had a solid content of 50% by weight. To the aqueous solution were portion-wise added, with agitation, 20.2 g(0.5 mole) of magnesium oxide to effect neutralization reaction. There was obtained the desired magnesium salt of boric acid ester of sorbitol. The thus obtained salt of the boric acid ester was a transparent, viscous liquid and easily soluble in water. The pH value of a 1 weight % aqueous solution of the salt was 7.2.

EXAMPLE 2

A mixture of 130 g(0.5 mole in terms of sorbitol) of SORBIT D-70 and 171 g(0.5 mole) of sucrose was heated, with agitation, at 100° C. to completely dissolve the sucrose therein. To the thus obtained uniform mixture were added 61.8 g(1 mole) of boric acid, and heating is then conducted at 115° C. for 3 hours to effect esterification with dehydration. The resulting ester was a light brown, viscous and water-soluble substance. The ester was diluted with water so as to have a solid content of 50% by weight, and then, 20.2 g(0.5 mole) of magnesium oxide were portion-wise added, with agitation, to effect neutralization reaction. There was obtained the desired magnesium salt of the boric acid ester which as also a light brown, viscous and water-soluble substance. The pH value of a 1 weight % aqueous solution of the salt was 8.4.

EXAMPLE 3

To 342 g(1 mole) of sucrose were added 170 ml of water, followed by heating to dissolve the sucrose in the water. To the resulting solution were added 61.8 g(1 mole) of boric acid and then, heating was conducted, with agitation, at 120° C. for 3 hours to effect esterification with dehydration. The resulting boric acid ester of sucrose was a brown, viscous and water-soluble substance.

The boric acid ester was diluted with water so as to have a solid content of 50% by weight, and was then neutralized with 47 g(0.5 mole in terms of MgO) of basic magnesium carbonate to obtain the desired magnesium salt of boric acid ester of sucrose which was brown and water-soluble. The pH value of a 1 weight % aqueous solution of the salt was 6.0.

EXAMPLE 4

The aqueous solution of the boric acid ester prepared in substantially the same manner as described in Example 1 was subjected to neutralization with 157.7 g(0.5 mole) of barium hydroxide (octahydrate) to obtain a water-soluble, transparent, viscous product which was the desired barium salt of the boric acid ester. The pH value of a 1 weight % aqueous solution of the barium salt was 7.9. The diluted aqueous solution of the barium salt was somewhat semi-turbid.

EXAMPLE 5

The aqueous solution of the boric acid ester prepared in substantially the same manner as described in Example 1 was subjected to neutralization with 37 g(0.5 mole) of calcium hydroxide to obtain an extremely water-soluble, transparent, viscous product which was the desired calcium salt of the boric acid ester. The pH value of a 1 weight % aqueous solution of the calcium salt was 7.9.

EXAMPLE 6

Substantially the same procedures of preparing a boric acid ester as described in Example 1 were repeated with the exception that 182 g of mannitol were used in place of 260 g of SORBIT D-70. There was obtained a boric acid ester of mannitol. The thus obtained boric acid ester of mannitol was diluted with water so as to have a solid content of 50% by weight. The resulting aqueous solution of the boric acid ester was subjected to neutralization with 157.7 g(0.5 mole) of barium hydroxide (octahydrate). The thus obtained barium salt of the boric acid ester was water-soluble. The pH value of a 1 weight % aqueous solution of the barium salt was 9.0.

EXAMPLE 7

An aqueous solution (solid content: 50% by weight) of a boric acid ester of mannitol prepared in substantially the same manner as described in Example 6 was subjected to neutralization with 20.2 g(0.5 mole) of magnesium oxide to obtain the desired magnesium salt of the boric acid ester of mannitol which was a water-soluble, light orange-colored, viscous liquid. The pH value of a 1% by weight aqueous solution of the magnesium salt was 8.8.

EXAMPLES 8 to 14

(1) Preparation of wet graphite particles as a carbonaceous material to be treated in accordance with the present invention 100 g of Madagascar-produced natural flake graphite particles having a bulk density of 0.81 and a sieve size of 50 to 80 mesh (Tyler) were dispersed in 400 g of 75% nitric acid, and then, 7 g of potassium permanganate were portion-wise added, while stirring, at 30° C. As the potassium permanganate was added as mentioned above, the temperature of the system rose to about 40° C. After the addition of magnesium permanganate, the system was heated, and maintained at 60° C. for 2 hours to accomplish oxidation reaction. The liquid in the system was removed by centrifugation, and subsequently the resulting graphite particles were washed with water so that the pH value thereof became 6.0. The thus washed graphite particles were dehydrated by centrifugation so that the water content thereof became about 30%. The resultant was employed as wet graphite particles to be treated in the instant Examples.

(2) Antioxidizing treatment

Using each of the metal salts of the boric acid esters obtained in Example 1 to 7, there were prepared seven kinds of aqueous solutions each having a solids concentration of 3% by weight.

Using each of the thus prepared aqueous solutions, antioxidizing treatment was carried out as follows.

100 g of wet graphite particles as prepared in the procedures of (1) above were dipped in 500 ml of an aqueous solution of the metal salt of the boric acid ester for 1 hour. The resulting soggy graphite particles were subjected to suction filtration so that the content of the aqueous solution was adjusted to 30% by weight.

(3) Preparation of graphite product and Test on oxidation-resistance

The graphite particles obtained in the procedures of (2) above were dried at temperatures below 100° C. and then heated in an electric furnace at 1,000° C. for 1 minute to obtain expanded, vermiform graphite masses having a bulk density of 0.012.

5 g of the vermiform graphite masses were charged into a 100 mm×150 mm metal mould and then compression-molded under a pressure of 100 Kg/cm² by means of a pressing machine. The compressed graphite masses were heated at 800° C. and further compressed under a pressure of 100 Kg/cm², followed by pressing by means of a constant speed roll so that the surface of the product was flattened and smoothened. There was obtained a flexible graphite sheet material having a thickness of 0.3 mm. Two sample pieces (30 mm×60 mm) of the flexible graphite sheet material were maintained, in an electric furnace for 4 hours, at 400° C. and at 600° C., respectively. From the weight difference between before and after the heat treatment, there was calculated an oxidation loss. Results are shown in Table 1.

COMPARATIVE EXAMPLE 1

Instead of the aqueous solutions of the metal salts of boric acid esters of saccharides according to the present invention, there was employed a 3 weight % aqueous solution of phosphoric acid. Except for the above, substantially the same procedures as described in Examples 8 to 14 were repeated to obtain a flexible graphite sheet. An oxidation loss of the sheet was examined in the same manner as in Examples 8 to 14. Results are also shown in Table 1.

COMPARATIVE EXAMPLE 2

Substantially the same procedures as described in Examples 8 to 14 were repeated except that the antioxidizing treatment was omitted and wet graphite particles as prepared in the procedures of (1) in Examples 8 to 14 were subjected directly to preparation of graphite product and test in substantially the same manner as described in the procedures (3) in Examples 8 to 14. Results are also shown in Table 1.

TABLE 1

| Example No. | No. of the Example in which the employed metal salt of boric acid ester was prepared | Oxidation loss, % 400° C./4hr | Oxidation loss, % 600° C./4hr | Tensile strength, Kg/cm² |
|---|---|---|---|---|
| 8 | Example 1 | 2.8 | 36.8 | 68 |
| 9 | Example 2 | 3.0 | 37.0 | 66 |
| 10 | Example 3 | 3.0 | 37.6 | 65 |
| 11 | Example 4 | 2.4 | 36.0 | 67 |
| 12 | Example 5 | 2.3 | 35.8 | 66 |
| 13 | Example 6 | 2.8 | 36.5 | 67 |
| 14 | Example 7 | 3.0 | 36.8 | 65 |
| Comparative Ex. 1 | — | 3.2 | 52.2 | 62 |
| Comparative Ex. 2 | — | 46.8 | 80.7 | 60 |

Note
Measurement of a tensile strength was done substantially according to the method prescribed in Japanese Industrial Standard (JIS) K-6301-1975, item 4.

EXAMPLES 15 to 17 AND COMPARATIVE EXAMPLE 3

A 12.5 mm×20 mm×32 mm piece of "TOHOSEI KOKUEN IG-11R" (tradename of a graphitized carbon manufactured and sold by Toyo Tanso Kabushiki Kaisha, Japan) was dipped, at room temperature for 1 hour, in a 3 weight % aqueous solution of a metal salt of boric acid ester of sorbitol as indicated in Table 2. The piece of graphitized carbon taken out of the above-mentioned aqueous solution was dried at 100° C. for 4 hours and then, the temperature was gradually elevated to 500° C. over about 4 hours to effect heat treatment of the graphitized carbon. The thus heat-treated piece of graphitized carbon was maintained in an electric furnace at 800° C. for 3 hours, and an oxidation loss was examined. Results are shown in Table 2.

On the other hand, for comparison, the same graphitized carbon as employed above was, without being treated with any antioxidant, put in an electric furnace and subjected directly to test on oxidation resistance in the same manner as described above. Results are also shown, as Comparative Example 3, in Table 2.

TABLE 2

| Example No. | Metal salt of boric acid ester of sorbitol | Oxidation loss, % |
|---|---|---|
| 15 | Mg salt | 21.7 |
| 16 | Ca salt | 20.8 |
| 17 | Ba salt | 21.0 |
| Comparative Ex. 3 | — | 60.5 |

What is claimed is:

1. An antioxidant for a carbonaceous material such as graphite or carbon which comprises at least one metal salt of a boric acid ester of a member selected from the group consisting of sorbitol, mannitol, sucrose, maltose, lactose and combinations thereof, said boric acid ester containing boric acid values in an amount of about 0.5 to 2.0 moles per mole of said member selected from the group consisting of sorbitol, mannitol, sucrose, maltose, lactose and combinations thereof, said metal being a member selected from the group consisting of magnesium, calcium, zinc and barium and being contained in an amount of about 1 to 3 atomic moles per mole of said boric acid ester.

2. A process for the preparation of an antioxidant for a carbonaceous material such as graphite or carbon which comprises the steps of (1) reacting a member selected from the group consisting of sorbitol, mannitol, sucrose, maltose, lactose and mixtures thereof with boric acid at about 105° to 130° C. for 2 to 5 hours, said boric acid being employed in an amount of about 0.5 to 2.0 moles per mole of said member selected from the group consisting of sorbitol, mannitol, sucrose, maltose, lactose and mixtures thereof, and (2) subsequently reacting the resulting boric acid ester with at least one compound of a metal selected from the group consisting of magnesium, calcium, zinc and barium at a temperature of about room temperature to about 100° C. for a sufficient time to complete the reaction, said compound of a metal being employed in an amount of about 1 to 3 moles in terms of amount of metal oxide per mole, in terms of amount of boric acid anhydride, of the boric acid ester.

3. A process according to claim 2, wherein said compound is a member selected from the group consisting of oxides, hydroxides, carbonates and basic carbonates of magnesium, calcium, zinc and barium.

4. A method of rendering graphite or carbon resistant to oxidation which comprises contacting graphite or carbon with an antioxidant comprising at least one metal salt of a boric acid ester of a member selected from the group consisting of sorbitol, mannitol, sucrose, maltose, lactose and combinations thereof for a sufficient time for said antioxidant to permeate the carbonaceous material, said boric acid ester containing boric acid values in an amount of about 0.5 to 2.0 moles per mole of said member selected from the group consisting of sorbitol, mannitol, sucrose, maltose, lactose and combinations thereof, said metal being a member selected from the group consisting of magnesium, calcium, zinc and barium and being contained in an amount of about 1 to 3 atomic moles per mole of said boric acid ester, ester, and subsequently subjecting said graphite or carbon to heat treatment at about 400° to about 1,300° C. for a sufficient time for said at least one metal salt to form a glassy compound.

5. A method according to claim 4, wherein said antioxidant is an aqueous solution of said at least one metal salt.

* * * * *

UNITED STATES PATENT AND TRADEMARK OFFICE
CERTIFICATE OF CORRECTION

PATENT NO. : 4,301,026
DATED : Nov. 17, 1981
INVENTOR(S) : Teruhisa Kondo et al

It is certified that error appears in the above-identified patent and that said Letters Patent are hereby corrected as shown below:

Title Page   Insert --Foreign Application Priority Data
Priority     December 2, 1978 Japan 53-148647--.

Signed and Sealed this

Fourth Day of May 1982

[SEAL]

Attest:

GERALD J. MOSSINGHOFF

Attesting Officer   Commissioner of Patents and Trademarks